(12) United States Patent
Zusman et al.

(10) Patent No.: US 7,732,659 B2
(45) Date of Patent: Jun. 8, 2010

(54) **INJECTING *DROSOPHILA* EMBRYOS**

(75) Inventors: Susan B. Zusman, Sudbury, MA (US);
Michael Tworoger, Somerville, MA (US)

(73) Assignee: Genetic Services, Inc., Cambridge, MA (US)

( * ) Notice: Subject to any disclaimer, the term of this patent is extended or adjusted under 35 U.S.C. 154(b) by 0 days.

(21) Appl. No.: 11/943,180

(22) Filed: Nov. 20, 2007

(65) Prior Publication Data

US 2009/0133140 A1 May 21, 2009

(51) Int. Cl.
*C12N 15/00* (2006.01)
*C12N 15/63* (2006.01)
*C12N 15/85* (2006.01)
*C07H 21/02* (2006.01)

(52) U.S. Cl. .................. 800/25; 536/23.1; 435/455
(58) Field of Classification Search .................. 800/25; 536/23.1; 435/455
See application file for complete search history.

(56) References Cited

U.S. PATENT DOCUMENTS

| | | | |
|---|---|---|---|
| 5,977,089 | A | 11/1999 | Arimilli |
| 6,005,087 | A | 12/1999 | Cook |
| 6,031,086 | A | 2/2000 | Switzer |
| 6,127,533 | A | 10/2000 | Cook |
| 6,225,460 | B1 | 5/2001 | Bischofberger |
| 6,399,754 | B1 | 6/2002 | Cook |
| 6,403,779 | B1 | 6/2002 | Kawasaki |
| 6,593,129 | B1 * | 7/2003 | Takeshita et al. ......... 435/285.1 |
| 2003/0175950 | A1 | 9/2003 | McSwiggen |
| 2004/0092470 | A1 | 5/2004 | Leonard et al. |
| 2004/0192626 | A1 | 9/2004 | McSwiggen et al. |
| 2005/0020525 | A1 | 1/2005 | McSwiggen et al. |
| 2005/0032733 | A1 | 2/2005 | McSwiggen et al. |
| 2006/0240409 | A1 * | 10/2006 | Prince et al. |

OTHER PUBLICATIONS

Baldarelli et al., 1990, Nucleic Acids Research, vol. 18, No. 19, 5903-5904.*
Robertson et al., 1988, Genetics, vol. 118, p. 461-470.*
Adams, et al., *Science*, 287:2185-2195, 2000.
Bateman, et al., *Genetics*, 173:769-777, 2006.
Beames, et al., *Virology*, 174:354, 1990.
Bellen, et al., *Genetics*, et al., 167:761-781, 2004.
Berg, et al., *Genetics*, 127:515-524, 1991.
Bischof, et al., *Proc. Natl. Acad. Sci., USA*, 104:3312-3317, 2007.
Celniker, et al., *Genome Biol.*, 3:RESEARCH0079, 2002.
Clark, et al., *Mol. Biol. Evol.*, 11:40-50, 1994.
Copeland, et al., *Nat. Rev. Genet.*, 2:769-779, 2001.
Daniels, et al., *Genetics*, 124:339-355, 1990.
Elick, et al., *Genetica*, 97:127-139, 1995.
Fish, et al., *Nat. Protocols*, 2:2325-2331, 2007.
Fraser, et al., *Virology*, 211:397-407, 1995.
Gelsthorpe, et al., *Genetics*, 174:265-270, 2006.
Golic, et al., *Nuc. Acid. Res.*, 25:3665-3671, 1997.
Grether, et al., *Genes and Development*, 9:1694-1708, 1995.
Grinblat, et al., *Development*, 120:91-102, 1994.
Groth, et al., *Genetics*, 166:1775-1782, 2004.
Groth, et al., *Proc. Natl. Acad. Sci., USA*, 97:5995-6000, 2000.
Haenlin, et al., *Cell*, 40:827-837, 1985.
Hagemann, et al., *Mol. Gen. Genet.*, 244:168-175, 1994.
Hall, *Drosophila Inform. Serv.*, 50:103, 1973.
Hoskins, et al., *Science*, 287:2271-2274, 2000.
Kimmerly, et al., *Genome Res.*, 6:414-430, 1996.
Lansman, et al., *Proc. Natl. Acad. Sci., USA*, 84:6491-6495, 1987.
Lee, et al., *Genomics*, 73:56, 2001.
Levis, et al., *Science*, 229:558-561, 1985.
Lisi, et al., *Genetics*, 154:669-678, 2000.
McEwen, et al., *Development*, 132:3935-3946, 2005.
Miller, et al., *Biotechniques*, 33:366-367, 2002.
Miller, et al., *Proc. Natl. Acad. Sci., USA*, 89:4018-4022, 1992.
Neuburger, et al., *Genetics*, 173:1377-1387, 2006.
Norga, et al., *Curr. Biol.*, 13:1388-1396, 2003.
O'Kane, et al., *Proc. Natl. Acad. Sci.*, 84:9123-9127, 1987.
Olivares, et al., *Nat. Biotechnol.*, 20:1124-1128, 2002.
Ortiz-Urda, et al., *Hum. Gene Ther.*, 14:923-928, 2003.
Ortiz-Urda, et al., *J. Clin. Invest.*, 111:251-255, 2003.
Ortiz-Urda, et al., *Nat. Med.*, 8:1166-1170, 2002.
Paricio, et al., *Nucleic Acids Res.*, 19:6713-6718, 1991.
Perkins, et al., *Proc. Natl. Acad. Sci., USA*, 89:10753-10757, 1992.
Rong, et al., *Genes Dev.*, 16:1568-1581, 2002.
Rong, et al., *Genetics*, 157:1307-1312, 2001.
Rong, et al., *Science*, 288:2013-2018, 2000.
Rubin, et al., *Science*, 218:348-353, 1982.
Shizuya, et al., *Proc. Natl. Acad. Sci., USA*, 89:8794-8797, 1992.
Siegal, et al., *Genetics*, 144:715-726, 1996.
Siegal, et al., *Methods Mol. Biol.*, 136:487-495, 2000.
Spradling, A. (1986) P-element mediated transformation in *Drosophila*, pp. 175-198 A Practical Approach by D. B. Roberts IRL Press.
Spradling, et al., *Genetics*, 153:135-177, 1999.
Spradling, et al., *Science*, 218:341-347, 1982.
Sternberg, et al., *Proc. Natl. Acad. Sci., USA*, 87:103-107, 1990.

(Continued)

*Primary Examiner*—Shin-Lin Chen
(74) *Attorney, Agent, or Firm*—Choate Hall & Stewart LLP; Brenda Herschbach Jarrell; Katherine Nicole Clouse

(57) ABSTRACT

The present invention provides systems that allow reliable multiplexed transformation of *Drosophila* embryos. The present invention provides methods and reagents that allow preparation of injection-quality nucleic acid samples and that allow simultaneous preparation of multiple such samples. The present invention provides systems for simultaneous processing of multiple injected embryos. The present invention provides methods for transformation of *Drosophila* embryos involving use of virginator strains that can be used to increase the efficiency of setting up the crosses needed to produce the eggs for the injections and for the crosses needed to screen for transformants.

13 Claims, No Drawings

OTHER PUBLICATIONS

Thorpe, et al., *Proc. Natl. Acad. Sci., USA*, 95:5505-5510, 1998.
Thyagarajan, et al., *Mol. Cell. Biol.*, 21:3926-3934, 2001.
Vagin, et al., *Science*, 313:320-324, 2006.
Venken, et al., *Science*, 314:1747-1751, 2006.
Wang, et al., *Insect. Mol. Biol.*, 1:109-116, 1993.
Wild, et al., *Genome Res.*, 12:1434-1444, 2002.
Wright, et al., *Drosophilia Information Service*, 87:108, 1974.
Baldarelli et al. "Transient expression of DNA after ballistic introduction into *Drosophilia* embryos" Nucleic Acids Research, vol. 18, No. 19, pp. 5903-5904, Aug. 27, 1990.
International Search Report for PCT/US2008/084250, mailed Sep. 22, 2009.
Qiagen Worldwide "For rapid, high-throughput purification of plasmid DNA from high-copy vectors" DirectPrep 96 Miniprep Handbook, Nov. 2003.
Spradling et al. "Transformation of Cloned P Elements into *Drosophila* Germ Line Chromosomes" *Science*, vol. 218:341-347, 1982.
Sullivan et al "Chapter 18: Quantitative Microinjection of *Drosophilia* Embryos" Cold Spring Harbor Laboratory Press, 2000, pp. 345-360.
Wieschaus, E. and Nüsslein-Volhard, C., *Drosophila: A Practical Approach*, p. 200, Roberts, D.B., ed., IRL Press, Oxford, England, 1986.
Written Opinion for PCT/US2008/084250, mailed Sep. 22, 2009.

\* cited by examiner

INJECTING *DROSOPHILA* EMBRYOS

BACKGROUND

In 1982, Gerald Rubin and Allan Spradling reported the development of a system for achieving genetic transformation of *Drosophila* by injecting embryos with transposable element vectors (see Spradling and Rubin, 1982, *Science*, 218:341; and Rubin and Spradling, 1982, *Science*, 218:348; both of which are incorporated herein by reference). This work remains one of the seminal developments in Molecular Biology. Indeed, a quarter century later, the technology for transforming *Drosophila* remains substantially unchanged.

Yet, there is room for improvement. Widely variable success rates are observed with different nucleic acid preparations, and the process is labor intensive. In general, only a few embryos can be processed at one time, so that "high throughput" *Drosophila* transformation is not possible.

Efforts are currently underway to automate certain steps in the *Drosophila* injection process; researchers have indicated that they hope to be able to achieve injection rates as high as 350 embryos in 2.5 hours if automated systems can be developed.

Thus, there is a need in the art for systems and methods for efficient injection of *Drosophila* embryos without the need for automation. There is a need in the art for systems and methods for injection of *Drosophila* embryos that increases the survival rate and the transformation rate of injected embryos.

SUMMARY

The present invention provides a system for rapid and efficient introduction of nucleic acids into *Drosophila* embryos, allowing reliable simultaneous processing of multiple embryos. Inventive systems can allow rapid processing of large numbers of embryos. For example, in some embodiments, the present invention provides multiplexed systems that allow injection of about 8 to 10 embryos every minute. In some embodiments, greater than 10 embryos (e.g. 11, 12, 13, 14, 15, 16, 17, 18, 19, 20, or more) embryos can be injected every minute (e.g. if multiple individuals simultaneously line up embryos for injection). In some embodiments, inventive multiplexed systems can achieve injection survival rates as high as about 50% percent of embryos injected. In some embodiments, fertility rates are as high as 85%-90% of injected survivors. In some embodiments, inventive multiplexed systems achieve injection transformation rates as high as about 80% of embryos injected.

In some embodiments, survival rates depend on the size of the nucleic acid being injected. In some embodiments, survival rates depend on whether transformation is attempted utilizing a nucleic acid that is randomly inserted into the genome (e.g. P-element-mediated insertion) or that is inserted into the genome in a site-specific manner (e.g. φC31-mediated transformation). For example, for nucleic acid constructs ranging from about 28 kb to about 30 kb, utilization of the φC31 integrase system in inventive multiplexed strategies can result in about 30%-about 70% of all injected embryos as fertile survivors. By contrast, those who utilize the φC31 integrase system with other transformation strategies typically report about 20%-about 50% of all injected embryos as fertile survivors.

Utilization of a P-element-mediated system and nucleic acids in the same size range in inventive multiplexed strategies can result in about 30% to about 70% of all injected embryos as fertile survivors. By contrast, those who utilize P-element-mediated systems with other transformation strategies typically report about 30% to about 50% of all injected embryos as fertile survivors.

For constructs even larger than about 30 kb, survival rate decreases for both random and site-specific transformation. However, the survival rate decreases more quickly for random insertion systems than for site-specific insertion systems.

For constructs smaller than about 28 kb, utilization of inventive strategies can result in about 30%-about 70% of all injected embryos as fertile survivors. By contrast, those who utilize other transformation systems typically report about 10%-about 50% of all injected embryos as fertile survivors.

For P-element constructs smaller than about 28 kb, utilization of inventive multiplexed strategies can result in about 30% of all injected embryos as transformants. Notably, utilization of traditional methods for P-element-mediated transformation can result in about 30% of all injected embryos as transformants. For P-element constructs larger than about 30 kb, inventive methods and/or traditional methods result in modest to significant decreases in transformation rates.

For integrase constructs of any size under about 40 kb, utilization of inventive multiplexed strategies can result in about 20% to about 85% of all injected embryos as transformants. Notably, utilization of traditional methods for integrase-mediated transformation can result in about 20% to about 80% of all injected embryos as transformants when integrase is provided in the form of a transgene (Bischof et al., 2007, *Proc. Natl. Acad. Sci., USA*, 104:3312; incorporated herein by reference). For integrase constructs of any size under about 40 kb, utilization of traditional strategies can result in about 10% of all injected embryos as transformants when integrase is provided in the form of an mRNA molecule (Venken et al., 2006, *Science*, 314:1747; incorporated herein by reference).

For integrase constructs larger than about 40 kb or about 50 kb, utilization of traditional methods for integrase-mediated transformation can result in about 2% to about 4% of all injected embryos as transformants when integrase is provided in the form of an mRNA molecule (Venken et al., 2006, *Science*, 314:1747; incorporated herein by reference). Utilizing integrase-mediated methods, constructs that are approximately 100 kb or even larger can be injected and can yield a significantly increased number of transformants (e.g. greater than 10%, 20%, 30%, 40%, 50%, 60%, 70%, or greater) using inventive multiplexed systems and methods.

Thus, the present invention provides systems and methods for transformation of *Drosophila* embryos that are faster, are more high-throughput, and can be performed on a larger-scale. The multiplexed systems and methods of the present invention result in equal or greater transformation frequencies than traditional (e.g. non-multiplexed) methods. The present invention provides systems and methods that allow for substantially increased efficiency (e.g. as measured by # transformants per minute of injection time) of transforming *Drosophila* embryos. The present invention represents a significant improvement over traditional methods.

In some embodiments, survival and transformation rates may depend on the particular nucleic acid being injected into *Drosophila* embryos. In some embodiments, transformation rate can depend on the nucleotide sequence of an injected construct. In some embodiments, transformation rate can depend on the vector nucleotide sequence. For example, the present invention encompasses the recognition that constructs having insulator sequences often have lower transformation rates than constructs not having insulator sequences. In some embodiments, transformation rate can depend on the nucleotide sequence that is inserted into a particular vector. For example, Nucleotide Sequence X inserted into a particular vector may transform more or less efficiently than Nucleotide Sequence Y inserted into the same vector. See Grinblat et al. (1994, *Development*, 120:91; incorporated herein by reference) for examples in which DNA sequence can affect transformation rates.

In some embodiments, methods for integrase-mediated transformation utilize injected mRNA for an integrase source (see, e.g., Groth et al., 2004, *Genetics*, 166:1775: and Fish et al., 2007, *Nat. Protocols*, 2:2325; both of which are incorporated herein by reference). In some embodiments, methods for integrase-mediated transformation utilize germline specific transposes for an integrase source (see, e.g., Bischoff et al, 2007, *Proc. Natl. Acad. Sci., USA*, 104:3312; incorporated herein by reference). The systems and methods of the present invention utilize a nanos-integrase transgene (Bischoff et al., 2007, *Proc. Natl. Acad. Sci., USA*, 104:3312; incorporated herein by reference). The present invention encompasses the recognition that providing integrase via a transgene expressing integrase results in higher transformation rates than providing integrase in the form of injected mRNA.

Among other things, the present invention provides methods and reagents that allow rapid and reliable preparation of injection-quality nucleic acid samples. Moreover, the present invention provides a multiplexed system for such nucleic acid preparation, so that a plurality (e.g., 96 or more) of injection-quality nucleic acid samples can be prepared at the same time.

The present invention also provides a system for large scale processing of DNAs in plates for the rapid processing of injected *Drosophila* embryos, and particularly provides methods and reagents for simultaneous transfer of a plurality of injected embryos to a growth medium sufficient to support hatching and initial larval development. Alternatively or additionally, in some embodiments "virginator" strains can be used to increase the efficiency of setting up the crosses needed to produce the eggs for the injections and for the crosses needed to screen for transformants.

DEFINITIONS

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

Injection-quality nucleic acids: As used herein, the term "injection-quality nucleic acids" refers to a preparation of nucleic acids that, when injected into *Drosophila* embryos prior to cellularization, allows for greater than 50% embryo survival. In general, injection-quality nucleic acids are characterized as being substantially free of alcohol (e.g. ethanol, isopropanol, etc.), RNA, proteins, and/or particulate matter and allowing for 25-50% survival or more of injected embryos.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, nucleic acids are DNA molecules that are injected into *Drosophila* embryos. In some embodiments, nucleic acids are injection-quality nucleic acids. In some embodiments, nucleic acids are not injection-quality nucleic acids.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Vector: As used herein, "vector" refers to a nucleic acid molecule capable of transporting another nucleic acid to which it has been linked. As used herein, the term "vector" generally refers to a nucleic acid molecule that is capable of integrating into a host cell's genome. In some embodiments, vectors integrate into a host cell's genome with the help of an enzyme (e.g. transposase, integrase, recombinase, etc.). Vectors capable of directing the expression of operatively linked genes are referred to herein as "expression vectors." In some embodiments, vectors direct expression of operatively linked genes once they have integrated into a host cell's genome. In some embodiments, vectors integrate randomly into a host cell's genome (e.g. P-element-based vectors). In some embodiments, vectors integrate at specific sites in a host cell's genome (e.g. integrase-mediated vectors). In some embodiments, vectors integrate into a host cell's genome for purposes of genetic transformation.

DESCRIPTION OF CERTAIN EMBODIMENTS

The present invention provides systems that allow reliable multiplexed transformation of *Drosophila* embryos. Among other things, the invention provides methods and reagents that allow preparation of injection-quality nucleic acid samples, and particularly that allow simultaneous preparation of multiple such samples. The present invention also provides systems for simultaneous processing of multiple injected embryos.

Transformation of *Drosophila* by Embryo Injection

In general, *Drosophila* transformation is a process in which exogenous DNA sequences are introduced into the *Drosophila* germ line. Any nucleic acid that can be integrated into the *Drosophila* germ line can be utilized in accordance with the present invention. Exemplary nucleic acid vectors that can be used for *Drosophila* transformation are presented in Table 1.

P-Element-Mediated Transformation

In some embodiments, *Drosophila* transformation is performed using P-elements. A P-element is a transposon that is present in *Drosophila melanogaster* and is used widely for mutagenesis and the creation of genetically modified flies. A P-element is a class II transposon, which means that its movement within the genome is made possible by a transposase. The complete element is 2907 bp and is autonomous because it encodes a functional transposase; non-autonomous P-elements which lack a functional transposase gene due to mutation also exist. Non-autonomous P-elements can still move within the genome if there are autonomous elements to produce transposase. A P-element can be identified by the presence of terminal 31-bp inverted repeats, and the 8 bp direct repeats in movement into and out of DNA sequence produces.

Naturally-occurring P-elements typically contain a coding sequence for the enzyme transposase and recognition sequences for transposase action. Transposase is an enzyme that regulates and catalyzes the excision of a P-element from the host DNA, cutting at two recognition sites, and then reinserts randomly. In general, to use P-elements as useful and controllable genetic tools, the two parts of a P-element are separated to prevent uncontrolled transposition. The normal genetic tools are, therefore, DNA coding for transposase with no transposase recognition sequences so it cannot insert, and a P-element construct. P-element constructs typically comprise a reporter useful for selecting transformants (e.g. white+, yellow+, etc.) and transposase recognition sequences. P-element constructs may further comprise a gene of interest, a bacterial reporter gene (e.g. gene encoding for antibiotic resistance), an origin of replication, etc.

P-elements containing constructs that are used for *Drosophila* transformation are often large DNA vectors. In some embodiments, P-elements containing constructs that are used for *Drosophila* transformation are at least about 10 kilobases (kb), at least about 15 kb, at least about 20 kb, at least about 25 kb, at least about 26 kb, at least about 27 kb, at least about 28 kb, at least about 29 kb, at least about 30 kb, at least about 31 kb, at least about 32 kb, at least about 33 kb, at least about 34 kb, at least about 35 kb, at least about 36 kb, at least about 37 kb, at least about 38 kb, at least about 39 kb, at least about 40 kb, at least about 41 kb, at least about 42 kb, at least about 43 kb, at least about 44 kb, at least about 45 kb, at least about 46 kb, at least about 47 kb, at least about 48 kb, at least about 49 kb, or at least about 50 kb (Haenlin et al., 1985, *Cell*, 40:827; incorporated herein by reference).

Site-Specific Transformation and Transformation of Large Nucleic Acids

While random P-element integration is useful for studies of gene function (O'Kane and Gehring, 1987, *Proc. Natl. Acad. Sci., USA*, 84:9123; and Spradling et al., 1999, *Genetics*, 153:135; both of which are incorporated herein by reference), position effects can strongly influence gene expression, complicating phenotypic analysis (Levis et al., 1985, *Science*, 229:558; incorporated herein by reference). Typically, more than 75% of P-elements insert in regulatory elements of genes (Bellen et al., 2004, *Genetics*, 167:761; incorporated herein by reference), often disrupting genes in subtle ways (Norga et al., 2003, *Curr. Biol.*, 13:1388; incorporated herein by reference). In some embodiments, therefore, it is desirable to be able to insert genes at the same chromosomal location. In some embodiments, *Drosophila* transformation is performed using systems and/or methods that allow for site-specific integration of exogenous nucleic acid material.

Additionally, current methods involving P-element-mediated transformation are limited by DNA size precluding the study of large genes (>40 kb) and gene complexes. In some embodiments, this is due to general difficulties in manipulating large DNA fragments. In some embodiments, this is due to difficulties in transferring large DNA fragments into the fly genome. In some embodiments, therefore, it is desirable to be able to transform *Drosophila* with large nucleic acid molecules. In some embodiments, *Drosophila* transformation is performed using systems and/or methods that allow for transformation of large nucleic acid molecules. In some embodiments, inventive strategies allow for successful transformation of *Drosophila* with P-element constructs larger than 40 kb (e.g. cosmids up to about 80 kb, [see, e.g., Lee et al., 2001, *Genomics*, 73:56; incorporated herein by reference]). In some embodiments, systems and/or methods that allow for site-specific integration also allow for transformation of large nucleic acid molecules.

In some embodiments, *Drosophila* transformation is performed using piggyBac elements. A piggyBac element is a short inverted terminal repeat (ITR) transposable element that is approximately 2.5 kb long and comprises 13-bp ITR sequences and a 2.1-kb ORF (Elick et al., 1995, *Genetica*, 97:127; and Beames and Summers, 1990, *Virology*, 174:354; both of which are incorporated herein by reference). It is part of a subclass of ITR elements that insert exclusively into TTAA target sites (Beames and Summers, 1990, *Virology*, 174:354; Fraser et al., 1995, *Virology*, 211:397; and Wang and Fraser, 1993, *Insect Mol. Biol.*, 1:109; all of which are incorporated herein by reference). On insertion, the target site is duplicated with excision occurring only in a precise fashion, restoring the insertion site. Beyond this functional similarity, the TTAA elements share no apparent structural identities. piggyBac vectors have been shown to mediate germ-line transformation in insect species.

A system involving Cre and FLP that allows for the study of two genes at identical places in the genome has been developed (Siegal and Hartl, 1996, *Genetics*, 144:715; and Siegal and Hartl, 2000, *Methods Mol. Biol.*, 136:487; both of which are incorporated herein by reference). In that system, a fly line is created by P-element insertion that contains the two transgenes of interest flanked by either loxP or FRT sequences. Under Cre expression, one transgene is removed, while under FLP expression, the other transgene is removed. Each remaining transgene is then left in the same chromosomal context.

In some embodiments, an approach to the site-specific integration problem is the use of homologous recombination. In general, the frequency of homologous recombination has been too low to be of practical use in *Drosophila*. However, in some embodiments, the frequency of homologous recombination can be boosted by using P-element transformation to insert a construct containing the gene to be targeted, engineered with an I-SceI cutting site and flanked by two FRT sites. This construct can then be mobilized as a circular DNA molecule by expression of FLP and made linear by the expression of I-SceI, increasing the targeted recombination frequency (Rong and Golic, 2000, *Science*, 288:2013; Rong and Golic, 2001, *Genetics*, 157:1307; and Rong et al., 2002, *Genes Dev.*, 16:1568; all of which are incorporated herein by reference). In this system, a separate P-element insertion carrying the homologous DNA engineered with I-SceI and FLP sites is required for each gene to be targeted. By this method, a targeted event could be obtained at a frequency of about 1 in 500-30,000 gametes from the female germline. Ideally, one could target an insertion to any position in the genome.

In some embodiments, the FLP/FRT system has been used in *Drosophila* to insert genes into any desired place in the genome. An integration frequency of up to 5% into a FRT site in the *Drosophila* genome can be obtained when the target DNA is mobilized from elsewhere in the genome by FLP excision (Golic et al., 1997, *Nuc. Acid. Res.*, 25:3665; incorporated herein by reference).

In some embodiments, *Drosophila* transformation is performed using integrase-mediated systems (see, e.g., Groth et al., 2004, *Genetics*, 166:1775; incorporated herein by reference). The site-specific integrase from phage φC31 (Thorpe and Smith, 1998, *Proc. Natl. Acad. Sci., USA*, 95:5505; incorporated herein by reference) has been shown to function at high frequency in human and mouse tissue culture cells and in vivo in mice (Groth et al, 2000, *Proc. Natl. Acad. Sci., USA*, 97:5995; Thyagarajan et al., 2001, *Mol. Cell. Biol.*, 21:3926; Olivares et al., 2002, *Nat. Biotechnol.*, 20:1124; Ortiz-Urda et al., 2002, *Nat. Med.*, 8:1166; Ortiz-Urda et al, 2003, *J. Clin. Invest.*, 111:251; and Ortiz-Urda et al, 2003, *Hum. Gene Ther.*, 14:923; all of which are incorporated herein by reference). The φC31 integrase requires no cofactors and mediates recombination between two sequences, the attB and attP sites, to create stable recombinants (Thorpe and Smith, 1998, *Proc. Natl. Acad. Sci., USA*, 95:5505; incorporated herein by reference). Both intra- and inter-molecular recombination occur at high frequencies, and essentially no reversion of the reaction occurs. It has been demonstrated that the integrase can recognize and integrate into endogenous pseudo attP sites in the human and mouse genomes that have partial identity to attP (Thyagarajan et al., 2001, *Mol. Cell. Biol.*, 21:3926; and Olivares et al., 2002, *Nat. Biotechnol.*, 20:1124; both of which are incorporated herein by reference). Mouse and human pseudo attP sites are typically 30%-45% identical to the wild-type attP.

In some embodiments, the φC31 integrase can mediate intra- and inter-molecular site-specific recombination at high frequency in *Drosophila*. In some embodiments, transgenic flies can be created in attP-containing fly lines by integrating an attB-containing plasmid injected along with integrase mRNA into *Drosophila* embryos.

As mentioned above, a limitation of P-element-mediated transformation is the inability to utilize large nucleic acid constructs. In general, cloning large DNA fragments in high-copy-number plasmids, such as typical P-element vectors, is inefficient because large fragments are unstable at high copy number in bacteria. Hence, low-copy-number vectors, including P1 (Sternberg, 1990, *Proc. Natl. Acad. Sci., USA*, 87:103; incorporated herein by reference) and bacterial artificial chromosome (BAC) (Shizuya et al., 1992, P *Proc. Natl. Acad. Sci., USA*, 89:8794; incorporated herein by reference) vectors, were developed to stably maintain large cloned DNA fragments. Unfortunately, low-copy-number vectors hamper sequencing, embryo injection, and other manipulations requiring large amounts of plasmid DNA. One solution that has been developed comprises a conditionally amplifiable plasmid that has two origins of replication (ori's): oriS for low-copy propagation, typical for P1 and BAC vectors; and oriV, which can be experimentally induced to high copy number (Wild et al., 2002, *Genome Res.*, 12:1434; incorporated herein by reference). Hence, conditionally amplifiable BAC features have been introduced into fly transformation vectors in order to facilitate the manipulation of large DNA fragments in *Drosophila*.

Cloning of large DNA fragments is limited by conventional methods that rely on restriction enzymes and DNA ligases, hampering analyses of large genes and gene complexes. Recently, efficient in vivo cloning technologies using enhanced and regulated recombination systems, commonly known as "recombineering," have been developed (Copeland et al., 2001, *Nat. Rev. Genet.*, 2:769; incorporated herein by reference). Recombineering facilitates the retrieval of DNA fragments through gap repair and their subsequent site-directed mutagenesis. Because recombineering is based on homologous recombination, restriction enzymes and DNA ligases are not required. Recombineering is widely used by mouse geneticists to generate transgenic and knockout constructs. Recombineering-mediated mutagenesis is more efficient with low-copy plasmids (Copeland et al., 2001, *Nat. Rev. Genet.*, 2:769; incorporated herein by reference). Hence, using recombineering in a conditionally amplifiable BAC has been shown to facilitate the gap repair of large DNA fragments and subsequent mutagenesis at low copy number.

Therefore, recombineering-based methods have been used to develop vectors that overcome the limitations associated with P-element-mediated transgenesis (Venken et al., 2006, *Science*, 314:1747; incorporated herein by reference). Venken et al. describe P/φC31 artificial chromosome for manipulation (P[acman]), a conditionally amplifiable BAC vector that contains recognition sites for both P-transposase—(Rubin and Spradling, 1982, *Science*, 218:348; incorporated herein by reference) and φC31-mediated integration (Groth et al., 2004, *Genetics*, 166:1775; incorporated herein by reference). P[acman] permits recombineering-mediated cloning of any genomic DNA fragment from *Drosophila* P1 or BAC clones (Kimmerly et al, 1996, *Genome Res.*, 6:414; Hoskins et al., 2000, *Science*, 287:2271; Adams et al., 2000, *Science*, 287:2185; and Celniker et al., 2002, *Genome Biol.* 3:RESEARCH0079; all of which are incorporated herein by reference) and enables the transfer of large DNA fragments into the fly genome. The ability to easily manipulate these DNA fragments through recombineering and to introduce them into specific sites in the fly genome can facilitate and accelerate in vivo genetic manipulations of *Drosophila*.

In some embodiments, P[acman] provides improvements when compared to current strategies for *Drosophila* transgenesis. In some embodiments, DNA constructs larger than 100 kb can be retrieved from genomic P1 and BAC clones using recombineering-mediated gap repair. Indeed, integration of fragments up to about 146 kb at defined sites has been reported (Bellen et al., 2006, 314:1747; incorporated herein by reference). Fragments are retrieved into a plasmid fitted with an inducible oriV replication origin that allows easy preparation of large quantities of DNA for sequencing and *Drosophila* transgenesis. Retrieved fragments do not need to be resequenced because they are directly retrieved from the genomic clone without PCR amplification. In some embodiments, unlike P-transposase, φC31-integrase enables the integration of large fragments into the *Drosophila* genome. Because φC31-integrase catalyzes recombination between two ectopic attachment sites (attB and attP), transgenes are integrated at specific docking sites in the fly genome. This largely eliminates the problem of position effects, a highly desirable feature when comparing different mutagenized constructs derived from the same transgene for structure/function analysis. In some embodiments, site-directed mutagenesis via recombineering is very efficient in low-copy plasmids such as P[acman].

In some embodiments, docking sites for site-specific integration systems can be characterized in more detail to determine the expression levels of different genes that are inserted in the same site. In some embodiments, it can be determined whether adjacent enhancers or regulatory elements influence gene expression in each of the docking sites in order to identify sites that are enhancing, suppressing, and/or "neutral." The neighboring genome environment may also become important when overexpression or RNA interference transgenes are inserted.

In some embodiments, the φC31 system can be optimized such that it achieves a level of efficiency, convenience, and expandability that renders it suitable for large-scale transgenesis approaches. In some embodiments, the system has been made to be more robust by improving the delivery of the φC31 integrase and to create a library of well characterized, highly efficient landing sites throughout the four major chromosomes of the *Drosophila* genome (Bischof et al., 2007, *Proc. Natl. Acad. Sci., USA*, 104:3312; incorporated herein by reference). Bischof et al. designed these landing sites so as to not interfere with commonly used markers and transposon systems, and to be manipulatable in vivo by the Cre/loxP and attP/attB systems. Different "endogenous" φC31 integrase sources were generated and optimized to overcome the need of coinjecting capped, in vitro synthesized integrase mRNA. These offer great flexibility regarding the choice of integration sites and the expression levels of transgenes. Predetermined integration sites effectively eliminate the time and effort needed to map transgene insertions, in contrast to those obtained by traditional transposon-mediated germ-line transformation. Defined attP sites allow precise in vivo structure/function analyses. In some embodiments, having a large collection of landing sites can facilitate the simultaneous use of multiple transgenes.

Additionally, Bischof et al. (2007, *Proc. Natl. Acad. Sci., USA*, 104:3312) describe the establishment of germ-line-specific φC31 integrases. The presence of an "endogenous" source of a transformation-mediating enzyme distinguishes this system from most other commonly used germ-line transformation methods for *Drosophila*. The use of a transgenic source of φC31 integrase eliminates the time and costs required for mRNA production and significantly reduces the complications associated with the injection process, such as the variability in efficiency caused by the quality and stability of the capped φC31 integrase mRNA. In some embodiments, such an "endogenous" integrase sources can considerably enhance the integration rates.

Bischof et al. (2007, *Proc. Natl. Acad. Sci., USA*, 104:3312) also describe an integration system that utilizes an immediate visible readout for specific attP targeting and therefore should permit rapid selection for precise integration events without having to perform a PCR reaction of each transformant. In particular, a large part of the white gene (exons 3-6) was placed into the landing site. The remaining part (promoter and exons 1-2) is provided by the transformation vector pw$^{P-Ex2}$UASTattB. Only if the incoming attB plasmid integrates into the donor attP site, located in the white intron between exons 2 and 3, will a functional white gene be reconstituted and result in the functional expression of white, indicating precise attP targeting. In addition to serving as an indicator for specificity, this split-white system reduces the size of the marker transgene and hence of the transformation vector, a property that can facilitate its handling and further increase the frequency of transgenesis.

Injection-Quality Nucleic Acids

It is well known that the quality of the nucleic acid preparation utilized in *Drosophila* embryo injections has a profound effect on the success of the injections, both in terms of survival rates and transformation rates. Most traditional DNA preparation methods involving double banded CsCl purification followed by ethanol precipitation. For example, Spradling and Rubin (1982, *Science*, 218:341; incorporated herein by reference) reported about 7.4% of injected embryos as transformants, and Rubin and Spradling (1982, *Science*, 218: 348) reported between about 0% and about 5% of injected embryos as transformants. Ashbumer (1989, *Drosophila, A Laboratory Manual*. Cold Spring Harbor Press, Cold Spring Harbor, N.Y.; incorporated herein by reference) and Spradling (1986, "P-Element-Mediated Transformation," pp. 175-197 in *Drosophila: A Practical Approach*, D. B. Roberts, ed. IRL Press, Oxford) described between 10% and 20% transformation rates utilizing double banded CsCl purified DNA.

Recently, more modern techniques (e.g., Qiagen purifications) have been used to purify DNA for P-element transformation (see, e.g., Gelstorpe et al., 2006, *Genetics*, 174:265; and Neuburger et al., 2006, *Genetics*, 173:1377; both of which are incorporated herein by reference). For example, utilizing the φC31 integrase system and more modern purification techniques, transformation rates of 16% to 55% have been reported (Groth et al., 2004, *Genetics*, 166:1775; and Bischof et al., 2007, *Proc. Natl. Acad. Sci., USA*, 104:3312; both of which are incorporated herein by reference).

The present invention encompasses the recognition that simultaneous preparation of multiple nucleic acid samples could increase the efficiency of *Drosophila* injection protocols. The present invention encompasses the recognition that traditional methods of simultaneously preparing multiple nucleic acid samples for injection do not result in production of injection-quality nucleic acids. As used herein, the term "injection-quality nucleic acids" refers to a preparation of nucleic acids that, when injected into *Drosophila* embryos prior to cellularization, allows for greater than 50% embryo survival. In general, injection-quality nucleic acids are characterized as being substantially free of alcohol (e.g. ethanol, isopropanol, etc.), RNA, proteins, and/or contaminating particles.

The present invention encompasses the recognition that high concentrations of nucleic acid are not required to achieve high transformation rates. In some embodiments, injection-quality nucleic acids are about 50 ng/μl, about 75 ng/μl, about 100 ng/μl, about 125 ng/μl, about 150 ng/μl, about 175 ng/μl, or about 200 ng/μl. In some embodiments, injection-quality nucleic acids range between about 50 ng/μl and about 100 ng/μl, between about 100 ng/μl and about 150 ng/μl, between about 150 ng/μl and about 200 ng/μl, between about 250 ng/μl and about 300 ng/µl, between about 300 ng/µl and about 400 ng/µl, between about 400 ng/µl and about 500 ng/µl, between about 500 ng/µl and about 600 ng/µl, between about 600 ng/µl and about 700 ng/µl, between about 700 ng/µl and about 800 ng/µl, between about 800 ng/µl and about 900 ng/µl, or between about 900 ng/µl and about 1000 ng/µl. The present invention encompasses the recognition that concentrations higher than 200 ng/µl can lead multiple insertions. In some embodiments, multiple insertions are not desirable. In some embodiments, multiple insertions are desirable.

In some embodiments, injection-quality nucleic acids comprise DNA vectors that are suitable for Drosophila transformation by injecting into embryos. Exemplary vectors that can be used for Drosophila transformation are included in Table 1.

TABLE 1

Exemplary Vectors Used for Drosophila Transformation

| Name | Synonyms | Features |
|---|---|---|
| pUAST | pP{UAST}<br>p[UAS] | white$^+$<br>P-elements<br>UAS enhancer<br>hsp70 promoter<br>SV40 3'UTR |
| pUC hsPI{Δ2-3} | | P-transposase |
| Carnegie 20 | pP{Car20}<br>pCy20 | P-elements<br>rosy$^+$ |
| Carnegie 4 | pP{Car4}<br>pCy4 | white$^+$<br>P-elements |
| CpLZ | pP{CPLZ} | lacZ gene |
| C4pLZ | pP{C4PLZ}<br>P{pC4PLZ}<br>P{C4PLZ} | P-elements<br>lacZ gene |
| pUAS-LacZN | UAS-lacZ<br>UAS-lacZN | white$^+$<br>P-elements<br>UAS enhancer<br>hsp70 promoter<br>SV40 3'UTR<br>nuclear lacZ |
| pGaTN | pGATN<br>pP{GaTN} | GAL4 gene<br>hsp70 3' sequence |
| pGaTB | pGATB<br>pP{GaTB} | GAL4 gene<br>hsp70 3' sequence |
| pYes | pP{YES}<br>pP{Y.E.S.}<br>Y.E.S | P-elements<br>gypsy insulators<br>su(Hw) binding regions |
| pExP | ExP<br>P{Express} | white$^+$<br>P-elements |
| pExp-3.5ey | P{Express-ey3.5} | white$^+$<br>P-elements |
| pExp-sev3x | P{Express-sev3x} | white$^+$<br>P-elements |
| αtub-pBac-K10 | A-tubulin pBac transposase | white$^+$<br>P-elements |
| pExp-VgMQ | P{Express-vgMQ} | white$^+$<br>P-elements |
| pCaSpeR 3 | pCaSpeR3<br>pP{CaSpeR-3} | white$^+$<br>P-elements |
| pUChsneo-act (BAM) | | white$^+$ |
| pUChsneo-act (R1) | | P-elements |
| P53R155H-pExP-gl | | white$^+$<br>P-elements |
| pCaSpeR-hs-act | P{CaSpeR-hs-act} | white$^+$<br>P-elements |
| pExp-UAS | P{Express-UAS} | white$^+$<br>P-elements<br>UAS enhancer |
| pExP-gl | P{Express-glass} | white$^+$<br>P-elements |
| pBUF | | ubiquitin promoter<br>ATG start codon<br>FLAG tag |
| pPac-PL | | white$^+$<br>P-elements |
| P53-pExp-gl | | white$^+$<br>P-elements |
| pCaSpeR-hs43-lacZ | | white$^+$<br>P-elements<br>lacZ gene<br>CaSpeR backbone |
| pC4βgal | | white$^+$<br>P-elements<br>βGAL Expression |
| pCaSpeR-βgal | | white$^+$<br>P-elements<br>βGAL expression<br>CaSpeR backbone<br>GAL4 gene |
| pC4CAT | | white$^+$<br>P-elements |
| pCaSpeR 1 | pP{CaSpeR-1}<br>pCaSpeR1 | white$^+$<br>P-elements |
| pCaSpeR 2 | pP{CaSpeR-2}<br>pCaSpeR2 | white$^+$<br>P-elements |
| pCaSpeR-hs | P{CaSpeR-hs} | white$^+$<br>P-elements<br>CaSpeR backbone |
| pUChsneo-act (RI) | | white$^+$<br>P-elements |
| pBUSH | | 6X His tag<br>ubiquitin promoter<br>ATG start codon |
| pBUHA | | ubiquitin promoter<br>ATG start codon<br>HA tag |
| pUAS-FLP | P{UAS-FLP1.B}<br>P{UAS-FLP1.D}<br>UAS > FLP | white$^+$<br>P-elements<br>UAS enhancer<br>hsp70 promoter<br>SV40 3'UTR<br>FLP recombinase gene |
| pPTGAL | | white$^+$<br>P-elements<br>GAL4 gene<br>minimal promoter<br>MCS for insertion of enhancer fragments |
| pUASP | | white$^+$<br>P-elements<br>UAS enhancer |
| pClasper | | white$^+$<br>P-elements |
| pCaSpeR AUG βgal | | white$^+$<br>P-elements<br>CaSpeR backbone |
| pUASM | | white$^+$<br>P-elements<br>UAS enhancer<br>hsp70 promoter<br>SV40 3'UTR<br>Modified Polylinker |
| XP | XPG | white$^+$<br>P-elements |
| warthog | WH, wartHog 5' | white$^+$<br>P-elements |
| razorBac | RB, pB3-razorBac-B | white$^+$<br>P-elements |
| piggyBac | PB, p3E1.2w$^+$, pB3 w$^+$ | white$^+$<br>can be used in D. simulans,<br>piggyBac elements |
| VEGF17E-A | | white$^+$<br>P-elements |
| VEGF27Ca | | white$^+$<br>P-elements |
| VEGF27Cb | | white$^+$<br>P-elements |
| VEGFR-A | | white$^+$<br>P-elements |

TABLE 1-continued

Exemplary Vectors Used for *Drosophila* Transformation

| Name | Synonyms | Features |
|---|---|---|
| VEGFR-B | | white+ |
| | | P-elements |
| VEGFR-C | | white+ |
| | | P-elements |
| pCaSpeR Act-R1 | P{CaSpeR-act(R)} | white+ |
| | P{CaSpeR-act} | P-elements |
| | | act5c promoter |
| pC3G4 | pCaSpeR-Gal4 | white+ |
| | | P-elements |
| | | GAL4 gene |
| | | hsp70 polyA+ |
| pCaSpeR Act-Bam | P{CaSpeR-act(B)} | white+ |
| | | P-elements |
| | | act5c promoter |
| pChs-GAL4 | | white+ |
| | | P-elements |
| | | GAL4 gene |
| | | hsp70 minimal promoter |
| | | hsp70 polyA+ |
| pP{Target} | | white+ |
| | | P-elements |
| | | I-CreI site |
| | | FRT sites |
| pP{TargetB} | | white+ |
| | | P-elements |
| | | I-CreI site |
| | | FRT sites |
| pUAST-Stinger | | white+ |
| | | P-elements |
| | | UAS enhancer |
| | | gypsy insulators |
| | | nuclear eGFP |
| pCaSpeR 4 | | white+ |
| | | P-elements |
| pRISE | pRISE-ftz | white+ |
| | | P-elements |
| | | SV40 3'UTR |
| | | Gateway cassette |
| | | UASt promoter |
| | | pUC8 backbone |
| | | ftz intron |
| pUASpGFP-Cnn | | white+ |
| | | P-elements |
| | | UAS enhancer |
| pGEM-S1 | | white+ |
| | | P-elements |
| pUASpEGFPc1 | | white+ |
| | | P-elements |
| | | UAS enhancer |
| pGD264 | pMF3 | white+ |
| | | P-elements |
| | | UAS enhancer |
| | | hsp70 promoter |
| | | SV40 3'UTR |
| | | pUC8 backbone |
| | | ftz intron#2 |
| pGEM-WIZ | | white+ |
| | | P-elements |
| | | used for RNAi experiments |
| pP{EndsOut2} | | white+ |
| | | hsp70 promoter |
| | | FRT sites |
| P[acman]-CmR | P[acman]-F-2 Pacman-CmR | white+ |
| | | P-elements |
| P[acman]-ApR | P[acman]-F-2-Amp-5 Pacman-ApR | white+ |
| | | P-elements |
| attB-P[acman]-CmR | P[acman]-F-2-attB | white+ |
| | | P-elements |
| | P[acman]-F-2-attB-2-4-2 attB-Pacman-CmR | attB sites used for φC31 integrase technology |
| attB-P[acman]-ApR | P[acman]-F-2-5-attB | white+ |
| | | P-elements |
| | P[acman]-F-2-Amp-5-attB-7-5-1 attB-Pacman-ApR | attB sites used for φC31 integrase technology |
| pET11phiC31polyA | | T7 promoter |
| | | lac operator |
| | | lacIq |
| | | T7 terminator |
| | | phiC31 integrase |
| pCaSpeR 5 | pP{CaSpeR-5} | white+ |
| | | P-elements |
| pUAS-C5 | pUAST-C5 | white+ |
| | | P-elements |
| | | UAS enhancer |
| | | hsp70 promoter |
| | | SV40 3'UTR |
| pGD264 | | white+ |
| | | P-elements |
| | | RNAi vector |

In some embodiments, exemplary vectors that can be used for *Drosophila* transformation are listed at https://dgrc.cgb.indiana.edu/vectors/store/vectors.html. One of ordinary skill in the art will recognize that this is an exemplary, not comprehensive, list of vectors. Any vector that is capable of transformation into *Drosophila* can be used in accordance with the present invention.

Nucleic acids in accordance with the present invention may comprise naturally occurring nucleosides, modified nucleosides, naturally occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. In some embodiments, nucleotides or modified nucleotides of a nucleic acid can be replaced with a hydrocarbon linker or a polyether linker provided that the functional characteristics of the nucleic acid are not substantially reduced by the substitution.

It will be appreciated by those of ordinary skill in the art that nucleic acids in accordance with the present invention may comprise nucleotides entirely of the types found in naturally occurring nucleic acids, or may instead include one or more nucleotide analogs or have a structure that otherwise differs from that of a naturally occurring nucleic acid. U.S. Pat. Nos. 6,403,779; 6,399,754; 6,225,460; 6,127,533; 6,031,086; 6,005,087; 5,977,089; and references therein (all of which are incorporated herein by reference) disclose a wide variety of specific nucleotide analogs and modifications that may be used in the preparation of synthetically produced nucleic acids. See Crooke, S. (ed.) *Antisense Drug Technology: Principles, Strategies, and Applications* (1$^{st}$ ed), Marcel Dekker; ISBN: 0824705661; 1st edition (2001) and references therein (incorporated herein by reference). For example, 2'-modifications include halo, alkoxy and allyloxy groups. In some embodiments, the 2'-OH group is replaced by a group selected from H, OR, R, halo, SH, $SR_1$, $NH_2$, $NH_R$, $NR_2$ or CN, wherein R is $C_1$-$C_6$ alkyl, alkenyl, or alkynyl, and halo is F, Cl, Br or I. Examples of modified linkages include phosphorothioate and 5'-N-phosphoramidite linkages.

Nucleic acids comprising a variety of different nucleotide analogs, modified backbones, or non-naturally occurring internucleoside linkages can be utilized in accordance with the present invention. Nucleic acids of the present invention may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. In some cases, nucleic acids comprising such modifications display improved properties relative to nucleic acids consisting only of naturally occurring nucleotides. In some embodiments, nucleic acid modifications described herein are utilized to reduce and/or prevent digestion by nucleases (e.g. exonucleases, endonucleases, etc.). For example, the structure of a linear nucleic acid may be stabilized by including nucleotide analogs at the 3' end of one or both strands order to reduce digestion.

Modified nucleic acids need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially affected. The modified region may be anywhere along the length of the nucleic acid molecule. One or both nucleic acid strands may comprise at least 50% unmodified nucleotides, at least 80% unmodified nucleotides, at least 90% unmodified nucleotides, or 100% unmodified nucleotides.

Nucleic acids in accordance with the present invention may, for example, comprise a modification to a sugar, nucleoside, or internucleoside linkage such as those described in U.S. Patent Publications 2003/0175950, 2004/0192626, 2004/0092470, 2005/0020525, and 2005/0032733 (all of which are incorporated herein by reference). The present invention encompasses the use of any nucleic acid having any one or more of the modification described therein. For example, a number of terminal conjugates, e.g., lipids such as cholesterol, lithocholic acid, aluric acid, or long alkyl branched chains have been reported to improve cellular uptake. Analogs and modifications may be tested, e.g., using any appropriate assay known in the art. In some embodiments, nucleic acids in accordance with the present invention may comprise one or more non-natural nucleoside linkages. In some embodiments, one or more internal nucleotides are inverted to yield linkages such as a 3'-3' linkage or a 5'-5' linkage.

Traditional Methods for Preparing Nucleic Acids for Injection

Traditional methods for preparing nucleic acids for injection frequently involve growing a microbial culture expressing the nucleic acid of interest, lysing the microbes, and using alcohol to precipitate the nucleic acid out of the cell lysate. In some embodiments, methods comprise a step of clearing the lysate prior to precipitation. In some cases, methods may further comprise filtration steps. In some embodiments, nucleic acids are prepared by ethidium bromide-CsCl gradient centrifugation.

Alternatively or additionally, there are several commercially-available systems for simultaneous preparation of multiple DNA samples (e.g. Qiagen, Millipore, etc.). These methods typically utilize 96-well plates and comprise either vacuum filtration or centrifugation to isolate and purify DNA.

For example, the QIAwell System consists of three independent multiwell modules which can be used separately or sequentially on the vacuum manifolds QIAvac 6S and QIAvac 96. In some embodiments, the procedure can also be automated on the BioRobot® 9600 and 3000.

Using the Qiagen system, plasmid DNA (e.g. DNA that has been purified using the miniprep procedures described in QIAwell® System Handbook for QIAwell 8 Ultra Plasmid Kit and QIAwell 96 Ultra Plasmid Kit, August 2001) is eluted from a QIAwell membrane with Buffer QE. Desalting and concentration take place in-line in a QIAprep module, which eliminates time-consuming precipitation and centrifugation. Double-stranded plasmid DNA binds to the silica-gel-based membrane of the QIAprep module; salts and other non-DNA constituents are efficiently removed by washing with Buffer PE. Pure plasmid DNA is eluted from QIAprep modules using Buffer EB. The eluted DNA typically ranges from 150 ng/µl to 200 ng/µl from a 5 ml LB culture. Optimum vacuum ranges between −200 mbar and −300 mbar for elution, and up to maximum vacuum for ethanol (Buffer PE) removal.

The Qiagen protocol is described in detail in the QIAwell® System Handbook (incorporated herein by reference). Briefly, nucleic acids are adsorbed to QIAprep membranes by applying a vacuum between −200 mbar and −300 mbar until all solutions have passed through. The vacuum is switched off, and each well is washed with 2×1 ml Buffer PE, using a vacuum between −200 mbar and −300 mbar. The vacuum is continued for 1 minute after complete transfer of Buffer PE. All traces of Buffer PE are removed by vigorously tapping the QIAprep plate on a stack of absorbent paper. If a 96-well-microplate centrifuge is available, a more convenient approach to remove ethanol may be centrifugation. A standard 96-well microplate is taped to the base of the QIAprep 96 plate and centrifuged at 1300×g for 1 minute.

The QIAprep 96 plate is placed back on the manifold, maximum vacuum is applied for 1 minute, ventilated, and the buffer removal procedure is repeated. Repeating the procedure will remove any droplets which have fallen from the walls of the wells in the first step. Vacuum and tapping steps are alternated until no further Buffer PE spots are observed on the absorbent paper. The QIAprep 96 plate is placed back on the manifold and maximum vacuum is applied for an additional 5 minutes. This step is meant to evaporate any remaining ethanol from the membranes.

The waste tray is removed and replaced with a microtube rack containing 1.2 ml collection microtubes. The manifold is reassembled, making sure that the QIAprep 96 plate and collection microtubes are properly aligned. 75 µl Buffer EB (10 mM Tris.Cl, pH 8.5) is added to the center of each well, and DNA is eluted by applying a vacuum between −200 mbar and −300 mbar for 30 seconds. The vacuum is increased to −600 mbar for 30 seconds. The vacuum cycle is repeated with another 75 µl buffer. Increasing the vacuum during elution will minimize the amount of elution buffer retained on the QIAprep membrane and maximize recovery of plasmid DNA. In some embodiments, DNA samples can be eluted into a microtiter plate using either QIAvac 96 or a microtiter plate centrifuge. To elute by centrifugation, a standard 96-well microplate is taped to the base of the QIAprep 96 plate and centrifuged for 1 minute at 1300×g. Using the QIAprep protocol, DNA yields of a high copy plasmid should be approximately 4 μg-5 μg per ml of starting culture. If plasmid DNA is to be concentrated by drying, DNA is eluted in 1 mM Tris.Cl, pH 8.5, or $H_2O$ with a pH>7.0.

Using the Millipore system, plasmid DNA (e.g. DNA that has been purified using the miniprep procedures described in Millipore MultiScreen® HTS PLASMID 96-Well Plates User Guide, September 2006; incorporated herein by reference) is eluted by applying a vacuum. The protocol is described in detail in the User Guide. Briefly, the MultiScreenHTS PLASMID plate is placed on top of the manifold collar. Full vacuum (24 inches of Hg) is applied for 5-7 minutes or until wells are empty. 200 μL of Milli-Q-grade water or Millipore Solution 4 is added to each well of the MultiScreenHTS PLASMID plate. Full vacuum is applied for 3-5 minutes or until wells are empty. To resuspend plasmid, 50 μL of Millipore Solution 5 is added to each well of the MultiScreenHTS PLASMID plate. To resuspend DNA, the plate is shaken for 5 minutes on a plate shaker. To recover DNA, retained plasmid is pipetted from the wells of the MultiScreenHTS PLASMID plate. To recover samples without shaking, the resuspension buffer is added to the wells, and the plate is allowed to sit for 30 minutes before pipetting.

Using the GeneScript system, plasmid DNA (e.g. DNA that has been purified using the miniprep procedures described in GeneScript QuickClean 96 Well Plasmid Miniprep Kit Manual, version 0712007; incorporated herein by reference) is eluted by centrifugation. The QuickClean 96-Well Plasmid Miniprep Kit is designed to purify up to 20 μg/well high-purity plasmid by centrifugation. Plasmid DNA is bound to the silica membrane plate, and the membrane is washed and the plasmid DNA is eluted in Elution Solution (Tris buffer) or water. The protocol is described in detail in the Miniprep Kit Manual. Briefly, the 96-Well Binding Plate is placed on top of the used 1.6 ml 96-Deep-Well Plate and centrifuged at 2,500×g for 5 minutes to bind the plasmid DNA on the membrane. The flow through is discarded. 500 μl of Wash Solution with ethanol is added to the 96-Well Binding Plate. The plate is centrifuged at 2,500×g for five minutes, and the flow through is discarded. The wash step is repeated.

The plate is centrifuged at 2,500×g for another five minutes to remove residual Wash Solution. The 96-Well Binding Plate is placed on top of a 96-Well Collection Plate. 50 μl of Elution Solution is transferred to the wells of the 96-Well-Binding Plate. The Elution Solution is allowed to incubate at room temperature for 1-2 minutes. The plate is centrifuged for 5 minutes at 2,500×g. The elution is repeated.

Preparation of Injection-Quality Nucleic Acids

The present invention encompasses the recognition that the traditional methods of preparing nucleic acids en masse (i.e. preparing a multitude of nucleic acid samples) for injection into *Drosophila* embryos, such as the methods described above, do not produce "injection quality nucleic acids."

In accordance with the present invention, all nucleic acid preparation steps are carried out at room temperature. In general, in accordance with the present invention, the following procedure is followed: a DNA sample is obtained, and the concentration is determined by standard methods (e.g. by measuring $OD_{260}$). About 1 ml of 5× PB is added to each well of a deep well plate, and about 5× volume of DNA (approximately 15 μg-approximately 20 μg) DNA is added to the PB. The PB-DNA solution is transferred into a 96-well vacuum plate (e.g. the QIAprep 96 plate). A vacuum is applied at approximately 100 mb. 1 ml of PE buffer (which contains about 80% ethanol) is added to each well to wash. A vacuum is applied to draw through most of the PE. The wash is repeated. The plate is transferred to waste collection tubes and centrifuged for 2 minutes at 3200 rpm (about 16,000×g). The present invention encompasses the recognition that this centrifugation step results in much more efficient removal of PE than vacuum alone. Next, a vacuboy is run over the top of the plates at about 100 mb to eliminate excess PE. The plates are dried at least 20 minutes (i.e. until all detectable traces of ethanol have evaporated). The series of drying steps differs from the drying steps of traditional protocols (e.g. Qiagen). The present invention encompasses the recognition that increasing the degree of drying substantially improves the quality of prepared nucleic acids. The present invention encompasses the recognition that spinning removes ethanol from the bottom of the plate, and the vacuboy removes ethanol from the top of the plate. The present invention encompasses the recognition that air drying further facilitates the removal of ethanol and significantly improves the quality of prepared nucleic acids.

For elution of DNA, the following procedure is followed: 50 μl of 1× injection buffer (0.1 mM sodium phosphate, 5 mM KCl; pH≧8) is added to each well and allowed to rest for one minute. The plates are centrifuged for 2 minutes at 3200 rpm (about 16,000×g). The flow through is discarded. The plates are transferred to clean collection tubes, and the elution is repeated a second and third time. This step differs from traditional protocols (e.g. Qiagen), which utilize only one elution. The present invention encompasses the recognition that multiple elutions allow for use of a significantly smaller elution volume than the minimum elution volume suggested by traditional methods (e.g. Qiagen). The present invention encompasses the recognition that performing multiple elutions results in improved quality of prepared nucleic acids (e.g. cleaner DNA). The flow through from the second and third elutions is saved. The present invention encompasses the recognition that centrifugation allows for much more efficient recovery of DNA than vacuuming into collection tubes. Quality and quantity of prepared nucleic acids are determined by standard agarose gel electrophoresis.

Simultaneous Processing of Multiple Injected Embryos

In the classic protocol described by Rubin & Spradling, injected embryos are placed in a moist chamber and allowed to hatch, at which point hatched larvae are individually removed and are transferred to standard fly food at 23° C.

Among other things, the present invention encompasses the recognition that individual transfer of hatchlings is labor intensive and risks damaging the larvae. The present inventors therefore developed a system in which embryos are removably affixed to a substrate for injection, and the substrate is then transferred to a food environment where hatching occurs.

Flies

In some embodiments, P-element-mediated transformation methods can be performed using any genus and/or species of Drosophilidae family. In some embodiments, P-element-mediated transformation methods can be performed using genera and/or species of families other than the Drosophilidae family. In some embodiments, P-element-mediated transformation methods can be performed using any member of the Diptera order. The present invention encompasses the recognition that integrase-mediated transformation methods can be performed using genera and/or species of families other than the Drosophilidae family. The present invention encompasses the recognition that integrase-mediated transformation methods can be performed using any member of the Diptera order.

In some embodiments, flies that are deficient in the allele that is to mark the transformants (e.g. $ry^{506}$, $w^{1118}$, yw, v, neomycin resistance, GFP and other fluorescent proteins, lacZ, etc.) are used to provide embryos for injection.

Embryo Collection

According to traditional injection methods, embryos for injection are collected using bottles of flies that are set up by taping an egg laying plate to the bottom of a plastic container in which holes have been poked using with a 20 gauge or smaller needle. According to many traditional protocols, bottles are moved to a day for night schedule at least two days before collections begin, as this is commonly thought to improve the number of eggs being laid. In contrast, the systems of the present invention utilize an egg-laying system in which acrylic tubing (e.g. about 2 inches to about 4 inches long) comprises mesh on one end of the tube and a grape plate on the other end. Also in contrast to traditional methods, the egg-laying apparatus is kept in constant darkness at all times, except for when an old grape plate is exchanged for a fresh plate. In accordance with the present invention, grape plates are generally produced as follows: 22.5 g agar is boiled in 750 ml water, being careful not to boil over. 1.5 g Nipigin and 25 g sucrose is boiled in 250 ml 100% grape juice, being careful not to boil over. Both mixtures are cooled to approximately 60° C. and combined. The resulting mixture is poured into petri plates (approximately 10 ml per plate).

In general, embryo collections are timed so that DNA is injected into each embryo before cellularization takes place. For example, in some embodiments, flies are allowed to lay eggs for ½ hour, and then the eggs and developing embryos are collected. The embryos are lined up for injection, which takes approximately ½ hour, and then injection takes about ½ hour. This timing is such that eggs are injected before cellularization occurs. According to traditional injection protocols, all steps after collection of eggs and embryos are typically carried out at 18° C. in order to slow down embryonic development. According to traditional injection methods, slowing down embryonic development ensures that eggs are injected before cellularization occurs. In contrast to traditional methods, the systems of the present invention involve keeping embryos at 20° C.-23° C. for all steps after collection of eggs and embryos. Utilizing the systems of the present invention, even at such temperatures, all eggs can be injected before cellularization occurs.

Preparing Embryos for Injection

Once embryos are collected, they are transferred to an adhesive surface (e.g. double stick tape or glue on a microscope slide). Embryos can be transferred using a damp fly brush, forceps, and/or a probe.

According to traditional injection methods, chorions are removed prior to injection. This is typically done in order to prevent the needle from breaking and/or clogging up. Chorions can be removed by lightly stroking embryos with forceps under dissecting microscope. Alternatively or additionally, chorions can be removed by treatment with bleach. For example, embryos can be treated with a solution of 50% bleach/water solution for 1-5 minutes. Embryos can be visually monitored to determine when chorions are removed, and therefore, when the incubation in the bleach solution should be stopped. After incubation with bleach, embryos are rinsed thoroughly with water to remove all residual bleach. In contrast, according to inventive systems, embryo chorions are not removed prior to injection. Instead, embryos are simply lined up, covered with oil, and injected. The present invention encompasses the unexpected observation that leaving chorions intact does not cause the needle to break and/or clog. The present invention encompasses the unexpected observation that injecting embryos with intact chorions helps to maintain good health of the embryos and can positively affect survival rate.

Embryos are lined up on an adhesive surface prior to injection. In general, embryos are lined up on the adhesive surface (e.g. microscope cover slide coated with tape or glue) such that their posterior ends point toward the edge of the substrate. Typically, the adhesive surface can be anything with sufficient adhesive properties such that embryos remain affixed to the surface throughout injection. The adhesive surface typically has sufficient rigidity to transport embryos to a food source after injection. In some embodiments, their posterior ends hang off of the edge of the adhesive surface. In some embodiments, their posterior ends do not reach the edge of the adhesive surface. According to inventive systems, eggs are lined up so that they are about ½ to about 1 egg length away from the edge of the slide. In some embodiments, a small ball of double stick tape is used to transfer embryos to an adhesive surface (e.g. double stick tape, glue, etc.). In some embodiments, a fly brush is used to transfer embryos to an adhesive surface. In general, the adhesive is non-toxic to the embryos and/or larvae that hatch from the embryos and does not negatively interfere with embryo survival.

According to traditional injection protocols, lined-up embryos are dessicated prior to injection. This has generally considered to be an important step for ensuring injection success. In particular, dessication has been considered a requirement to prevent embryos from leaking immediately upon being injected. Dessication protocols typically involve placing the adhesive surface to which embryos are affixed in a dish containing Drierite for 5-15 minutes. In contrast, inventive injection methods do not include a dessication step. The present invention encompasses the surprising recognition that embryos do not need to be dessicated in order to achieve high survival and/or transformation rates. The present invention encompasses the surprising recognition that embryo health can be improved by omitting the dessication step.

According to traditional methods, after dessication, embryos are typically covered with halocarbon oil (e.g. mixture of series HC-700 and series 27 at a 7:1 ratio, respectively) and mounted on the stage of an inverted microscope that is connected to a microinjector. In contrast, inventive injection methods involve the use of a stereomicroscope that is connected to a microinjector.

Injection Apparatus

According to traditional methods, the injection apparatus comprises an inverted microscope equipped with a 20× lens, a micromanipulator, and an air-pressure injecting device (e.g., Narishige IM-300 Microinjector) connected to the needle holder. In some traditional methods, bright field or Nomarski microscopy is used to monitor injections. In contrast, inventive injection methods utilize a stereomicroscope (e.g. Picospitzer by General Valve, Inc.) to monitor injections.

According to traditional methods, the injection apparatus is in an 18° C. room, which gives more time flexibility as the embryos develop more slowly and the appropriate stage for injection lasts longer. In contrast, the systems of the present invention involve housing the injection apparatus in a 20° C.-23° C. room. The present invention encompasses the recognition that, even at such temperatures, all eggs can be injected before they develop beyond the appropriate stage for injection.

Needles

In some embodiments, needles are made from siliconized glass. In some embodiments, needles are pulled to a tip diameter of less than approximately 1 μm. In some embodiments, needles that are suitable for embryo injection comprise an approximately 1 mm capillary.

According to traditional injection methods, needles can be pulled on any horizontal puller. For example, needles can be pulled on any horizontal puller of the Sutter brand series using 1.0 mm OD borosilicate capillaries with omega dot fiber (e.g. Frederick Haer & Co, #30-30-0). The settings will be different for each machine and usually need to be updated each time the heating filament is replaced or re-shaped or when a new type of capillary is used. In contrast, according to inventive systems, needles are pulled using a vertical needle puller. In particular, Kopf Instruments Model 720 is utilized in accordance with inventive systems.

Several parameters influence the shape and properties of the needle (e.g. heat, velocity of pull, pressure of gas flow, number of steps). In some cases, the effect of adjusting any of these parameters on the properties of the resulting needle can be difficult to predict. A paper by Miller et al. (2002, *Biotechniques*, 33:366; incorporated herein by reference) describes some useful guidelines for designing suitable needles. In some embodiments, a needle for embryo injection should be progressively but shortly tapered and have no discontinuity or step. In general, needles that are too elongated may bend and break when attempting to pierce the embryo. Needles that are too blunt, on the other hand, do not tend to bend, but can damage the embryos more severely and lower the overall survival rate. Once the needles are suitable to penetrate the embryos smoothly, the amount of injection mix coming out can be adjusted by playing with the injection time (e.g. between 10 ms and 40 ms) and the pressure knobs ($P_{out}$ and $P_{balance}$).

Needles are typically back-filled. Needles can be loaded using a long, stretched-out pipette tip, such as the pipette tips that are used to load sequencing gels. In most cases, a needle is loaded with a few microliters of injection-quality nucleic acid. Once injection-quality nucleic acid has been loaded into the needle, the needle can be mounted into the injection apparatus.

According to traditional methods, once the needle has been loaded with nucleic acid, the tip of the needle is broken to create an opening in the tip prior to injection of the first embryo. There are many techniques available for breaking the tip of the needle. In some embodiments, the tip of a needle can be broken by running the tip through halocarbon oil into the layer of double stick tape on the adhesive surface. Alternatively, the tip of a needle can be broken by beveling the tip using a slurry of grinding powder and a regular magnetic stirring set-up. The slurry is made from silicon carbide powder and ddH$_2$O at a 1:3 ratio. The grit should be washed several times to remove small particles that can remain suspended after the bulk has settled out. While the slurry is being stirred, the tip of the pipette is inserted at a 135° angle with respect to the direction of flow of the slurry. By holding the needle steady for 4-5 minutes, the tip of the needle becomes beveled to a sharp point. In some embodiments, the tip of a needle can be broken by gently touching the tip of the needle to the edge of a slide under a microscope while applying gentle positive pressure. In contrast, according to inventive systems, the needle is not broken prior to injection of the first embryo. According to inventive systems, the needle is broken upon injection of the first embryo.

Injecting Embryos

Before injecting into embryos, expel air from the needle until the nucleic acid solution begins flowing into the oil covering the embryos. Embryos are typically injected by piercing their posterior ends, drawing the needle back as far as possible while still inside, and expelling the injection-quality nucleic acid solution into the embryos. According to traditional methods, approximately 1%, approximately 2%, approximately 3%, approximately 4%, approximately 5%, or more than approximately 5% of embryo volume should be expelled into each embryo. In contrast, according to inventive systems, about a volume corresponding to about ¼ to about ½ of embryo diameter is expelled into each embryo.

After all of the embryos in a single round have been injected, damaged and/or improperly aged embryos can be removed.

After injection, embryos are placed in on moist medium and allowed to hatch. For example, in some embodiments, embryos are transferred to a food source. In some embodiments, embryos are transferred to an apple juice or grape juice plate on which a solution of yeast (i.e. *Saccharomyces cerevisiae*) has been streaked. According to traditional methods, embryos are individually removed from the adhesive surface and placed directly on the food source. In contrast, according to inventive systems, the entire adhesive surface on which embryos are affixed is placed on a food source. After larvae hatch, they are able to crawl to the food, and survivors are allowed to grow to adulthood.

Fly Crosses

The rate at which *Drosophila melanogaster* develops is largely dependent on environmental temperature. At 25° C., about one day after fertilization, an embryo has fully developed and hatched into a larva. The larva eats and grows continuously, molting one day, two days, and four days after hatching (first, second, and third instars, respectively). After two days as a third instar larva, it molts one more time to form an immobile pupa. Over the next four days, the body is undergoes metamorphosis to give the adult winged form, which then hatches from the pupal case (i.e. "eclosion"). Development takes approximately twice as long at 18° C. than at 25° C.

Identifying and Mapping Transformants

Typically, for P-element-mediated transformation, embryos that survive the injection process are individually backcrossed to the injection stock. For φC31 integrase-mediated transformation, embryos that survive are individually backcrossed to flies carrying a mutation (e.g. $w^{1118}$). This step is performed because not every insertion is into germline cells, but some insertions are into somatic cells. Outcrossing selects for lines that have germline insertions and are able to pass the exogenous nucleic acid onto its progeny. Backcrossing to the injection stock is often performed twice to ensure the selection of stable germline transformants.

In some embodiments, after injection, each F0 female is crossed with at least two males of the parental strain, while each male is crossed with at least two virgin females of the parental strain. Transformants are screened in the progeny of these single mates. To give but one example, consider a case in which an exogenous nucleic acid which expresses a gene that causes pigment to be expressed in the eye was injected into a white-eyed stock (e.g. $w^{1118}$):

1) No F1 individuals from a single cross display pigment in the eye. This typically indicates no transformants.
2) Some F1 individuals (e.g. less than 10%) display pigment in the eye. If every female displays the same eye color that is lighter than pigmented males, it is likely that this tube will give a single transgenic line.

3) Many F1 individuals (more than 50%) display various eye colors. This is often indicative of a multiple insertion. Depending on the situation, individuals displaying the lighter eye color should be selected for further crosses. In some embodiments, multiple insertions are not desirable. In some embodiments, individual flies displaying stronger eye color may be discarded, as they often bear multiple insertions.

F1 individuals may bear one or more transgene insertion(s) on any of the X chromosome, chromosome II, or chromosome III. Transgenes inserted on chromosome IV are very rare as this chromosome is rather small and essentially heterochromatic. In some embodiments, transgenes are integrated on chromosome IV at a rate of less than approximately 5%. In some embodiments, transgenes are integrated on chromosome IV at a rate of approximately 1%. In some embodiments, F1 flies are crossed to balancer stocks. In some embodiments, F1 flies are crossed to $w^{118}$ flies. In some embodiments, a single male F1 transformant is crossed to a balancer stock or to a $w^{118}$ stock. In some embodiments, a single female F1 transformant is crossed to a balancer stock or to a $w^{118}$ stock. In general, setting up single crosses can reduce the probability of multiple inserts.

Once a line is identified that appears to be transgenic, the stock containing the transgene is typically crossed to a balancer stock to avoid loss of the transgene due to recombination events during meiosis.

Efficient Virgin Collection

Female flies can store enough sperm for a lifetime's worth of eggs, so when setting up crosses, virgin females must be used. In order to collect virgins, female flies must be isolated from male flies before they have reached sexual maturity. Females remain virgins for about 6 hours-8 hours at 25° C., and for 16 hours-18 hours at 18° C. In some embodiments, virgins can are collected by use of a twice a day procedure in which vials/bottles are cleared in the morning, placed at 25° C. for about 6 hours, the females (who should all be virgins) are collected and the vials/bottles are placed at 18° C. overnight, and females/virgins are collected again the following morning. If a collection is missed, or if only a few virgins are needed for a particular cross, virgins can be identified by the presence of a dark spot in their abdomens.

To collect virgin females, vials of flies at 25° C. are typically checked every 6-8 hours, and female flies are separated from male flies. Vials of flies at 18° C. are typically checked every 10 hours-12 hours, and female flies are separated from male flies.

In some cases, females can be isolated by visually examining pupae. Flies that display female physical characteristics instead of male physical characteristics can be identified and placed into a separate vial of food before eclosing. Thus, the only flies that eclose in that vial of food are females, and, therefore, virgins.

In some embodiments, "virginator" stocks can be used to simplify the process of collecting virgins. Virginator stocks are typically fly stocks for which only females survive to adulthood. In general, any stock carrying a transgene that causes lethality when expressed under the control of an inducible promoter on the Y chromosome is a virginator stock in accordance with the present invention. For example, the hs-hid virginator stock is characterized by the presence of a heat-shock (hs) hid construct on the Y chromosome. When larvae are subjected to heat shock (e.g. 37° C.), hid is overexpressed in males, resulting in lethality. To give another example, another virginator stock carries a temperature-sensitive lethal mutation, shibire-ts ($shi^{ts}$), on the male X chromosome (Hall, L, 1973, Drosophila Inform. Serv., 50:103; incorporated herein by reference). When grown at 30° C. during the pupal stage, the $shi^{ts}$ males die, leaving bottles from which only females hatch. Some exemplary virginator stocks are presented in Table 2.

TABLE 2

Exemplary Virginator Stocks

| Stock | Genotype | Description |
|---|---|---|
| hs-hid (BL-8846) | $y^1$ w*; Dp(2;Y)G, P{hs-hid}Y | heat shock of larvae at 37° C. results in overexpression of hid and male lethality |
| $shi^{ts}$ (BL-1512) | $y^2$ $ras^1$ $v^1$ $RpII215^1$ $shi^1$/FM7a, Df(1)FM7, l(1)**/Dp(1;Y)$y^+v^+$ #3 | incubation of pupae at 30° C. results in male lethality |
| DTS513 | T (Y; 2)CyO, DTS513 | growth at 29° C. results in male lethality (Wright and Green, 1974, Drosophila Inform. Serv. 87: 108; incorporated herein by reference) |

Applications

The systems and methods of the present invention can be used to introduce any exogenous nucleic acid into any Drosophila species. In some embodiments, the systems and methods of the present invention can be used to introduce any exogenous nucleic acid into any member of the Diptera order. In some embodiments, methods of the present invention can be used to drive expression of one or more heterologous nucleic acids (e.g. protein-encoding genes) in Drosophila. In some embodiments, a heterologous nucleic acid sequence is a nucleic acid sequence that is present in the Drosophila genome. In some embodiments, a heterologous nucleic acid sequence is a nucleic acid sequence that is not present in the Drosophila genome.

In some embodiments, expression can be driven using a constitutive promoter. For example, a nucleic acid construct can be prepared which comprises a constitutive promoter (e.g. actin promoter) translationally fused to a heterologous nucleic acid sequence (e.g. a protein-encoding gene). For the purposes of this example, such a construct will be referred to as "act-GeneX." Flies transgenic for act-GeneX express GeneX from the constitutive act promoter.

In some embodiments, expression can be driven using a conditional promoter. Conditional promoters allow for spatial and/or temporal control of transgene expression. For example, a nucleic acid construct can be prepared which comprises a Gal4 recognition sequence (e.g. upstream activating sequence, or "UAS") translationally fused to a heterologous nucleic acid sequence (e.g. a protein-encoding gene). For the purposes of this example, such a construct will be referred to as "UAS-GeneX." When a strain of flies transgenic for UAS-GeneX is crossed to flies expressing Gal4, GeneX, which is under UAS control, is expressed in the progeny of the cross.

In some embodiments, methods of the present invention can be used for expressing tagged constructs in Drosophila. To give but one example, a nucleic acid construct may comprise a protein-encoding gene that is tagged with an affinity tag (e.g. 6× His tag, FLAG tag, GST tag, etc.) under the control of a constitutive or conditional promoter, as described above. In some embodiments, the affinity tag is at the 5' of the gene sequence. In some embodiments, the affinity tag is at the 3' of the gene sequence. In some embodiments, the affinity tag is in the middle of the gene sequence. In some embodiments, the affinity tag allows for efficient purification of the expressed gene product. In some embodiments, the affinity tag allows for visualization of the expressed gene product (e.g. by immunohistochemistry using antibodies that recognize the affinity tag).

In some embodiments, methods of the present invention can be used for inducing mutations in *Drosophila*. For example, a transgene can be introduced which drives the expression of a gene that is normally present in *Drosophila*, but carries one or more mutations.

In some embodiments, methods of the present invention can be used for insertional mutagenesis. In some cases, nucleic acids (e.g. P-elements) are integrated into the genome in positions that disrupt the expression of a gene. This could occur if a nucleic acid integrates into the coding sequence or into a regulatory sequence of a gene.

In some embodiments, methods of the present invention can be used for developing *Drosophila* models for human disease. For example, fly models can be generated and then small molecule drug screening can be performed or genetic screens for modifiers of the phenotype can be performed.

In some embodiments, methods of the present invention can be used to study human disease. Despite the differences in complexity between *Drosophila* and humans, genomic analysis has confirmed that many key proteins involved in a multitude of processes and the functional mechanisms that they govern are remarkably similar. Indeed, *Drosophila* species have approximately 60% of all human genes. Based on these similarities, *Drosophila* has been shown to serve as a model system for studying human disease. In some embodiments, a *Drosophila* model for a human disease may contain one or more mutations in one or more fly genes known to be associated with the disease in humans. In some embodiments, a *Drosophila* model for human disease may contain one or more mutations that result in phenotypes in flies similar to phenotypes associated with the disease in humans. Several working *Drosophila* models for human disease are currently known, examples of which include, but are not limited to, polyQ diseases, such as SCA1 (expression of pathogenic form of ataxin 1), MJD/SCA3 (expression of pathogenic form of ataxin 3), Kennedy's Disease (mutation in androgen receptor), and Huntington's Disease (affects poly Q pathology; mutation affects huntingtin protein); Spinal muscular atrophy (caused by a mutation in human survival motor neurons 1 (SMN1) gene); Alzheimer's Disease (expression of neurodegenerative disease-associated form of the human protein tau, β-amyloid, and/or presenillins); Parkinson's Disease (mutation in α-synuclein gene, such as the A53T and/or A30P mutations); obesity (e.g. a mutation in the adipose gene cause fat flies); diabetes (mutation affecting the insulin pathway); amyotrophic lateral sclerosis (Lou Gehrig's Disease; copper/zinc superoxide dismutase mutants); and epilepsy (mutations in $K^+$ channel genes).

In some embodiments, *Drosophila* disease models can be useful in the screening of therapeutic agents to treat the disease. For example, *Drosophila* models can be useful for screening small molecule drug libraries to identify substances that may be therapeutically effective in humans.

In some embodiments, a *Drosophila* model may be used as a genetic background for which to perform a genetic screen. By monitoring the disease phenotype, the screen can identify genes that are associated with the disease phenotype in flies. For example, such a screen can identify enhancers and/or suppressors of the disease phenotype. Once they are identified, the role of these genes in the human disease can be analyzed.

EXEMPLIFICATION

Example 1

Simultaneous Preparation of 96 Samples of Injection-Quality Nucleic Acid

All steps are carried out at room temperature. A DNA sample is obtained, and the concentration is determined by standard methods (e.g. by measuring $OD_{260}$). About 1 ml of 5× PB (contains isopropanol and guanidinium-HCl) is added to each well of a deep well plate, and about 5× volume of DNA (approximately 15 µg-approximately 20 µg) DNA is added to the PB. The PB-DNA solution is transferred into a 96-well vacuum plate (e.g. the QIAprep 96 plate). A vacuum is applied at approximately 100 mb. 1 ml of PE buffer (which contains about 80% ethanol) is added to each well to wash. A vacuum is applied to draw through most of the PE. The wash is repeated. The plate is transferred to waste collection tubes and centrifuged for 2 minutes at 3200 rpm (about 16,000×g). The present invention encompasses the recognition that this centrifugation step results in much more efficient removal of PE than vacuum alone. Next, a vacuboy is run over the top of the plates at about 100 mb to eliminate excess PE. The plates are dried at least 20 minutes (i.e. until all detectable amounts of ethanol have evaporated).

For elution, 50 µl of 1× injection buffer (0.1 mM sodium phosphate, 5 mM KCl; pH≧8) is added to each well and allowed to rest for one minute. The plates are centrifuged for 2 minutes at 3200 rpm (about 16,000×g). The flow through is discarded. The plates are transferred to clean collection tubes, and the elution is repeated a second and third time. The flow through from the second and third elutions is saved. The present invention encompasses the recognition that centrifugation allows for much more efficient recovery of DNA than vacuuming into collection tubes. Verify the quality and quantity of DNA purified by standard agarose gel electrophoresis.

Example 2

Injection of Embryos

A microcentrifuge tube is spun in a centrifuge for 2 minutes at 13,200 rpm (approximately 16,000×g). 0.5 µl of DNA is loaded into a borosilicate capillary pulled needle using a microloader. A 3 mm×1.5 cm piece of Scotch® Removable Poster Tape (product #109) is attached to a standard glass microscope slide. Egg-laying is allowed to occur for 30 minutes onto an agar-grape plate. Eggs are transferred within the following 30 minutes onto the double-sided tape, leaving 0.5 mm space between the eggs. Eggs are oriented such that their posterior ends are pointing toward one edge of the slide. Eggs are covered with halocarbon oil. Eggs are injected with loaded DNA using injection setup comprising a Zeiss stereomicroscope, General Valve Picoscpritzer III injector, and a Narishige MN-153 micromanipulator. Use DNA droplets 0.2×-0.33× the width of the egg. Using a sharp razor blade, double-sided tape with injected eggs is detached from the slide and placed in a vial of fly food, orienting eggs up.

Example 3

Efficient Collection of Virgin Flies

In some embodiments, virgin female flies are collected using the hs-hid virginator stock. Flies from the hs-hid stock are allowed to mate for 3 days at 25° C. At the end of day 3, adult flies are emptied out of the vials. On day 4, vials with larvae are heat shocked (e.g. incubated in a 37° C. water bath for 2 hours). After 2 hours, vials are returned to the 25° C. incubator. On day 5, heat shock is repeated. Flies are incubated at 25° C. until virgin females begin to eclose (e.g. about one week). Adult virgins are collected.

Example 4

Rapid, Multiplexed Process for Efficient Generation of Transgenic *Drosophila*

A 96-well plate comprising about 50 different DNA preparations was used for injection of embryos. Each DNA preparation comprised a construct for injection using φC31 integrase technology and a Gateway® vector (Invitrogen, Inc., Carlsbad, Calif.). Each injection construct was approximately 12 kb in size. About 50-about 100 embryos per construct were injected in about 10 hours.

After injection, about 50% of injected embryos survived to adulthood. Of these, about 85% were fertile and about 72% were transformants.

EQUIVALENTS AND SCOPE

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Thus, for example, reference to "a nanoparticle" includes a plurality of such nanoparticle, and reference to "the cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any characteristic of injection-quality nucleic acids, any method of preparing injection-quality nucleic acids, any method of injecting embryos, any *Drosophila* species, any therapeutic application, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

We claim:

1. A method comprising steps of:
  obtaining a plurality of different nucleic acid samples for injection by needle into *Drosophila* embryos; and
  injecting at least 8 embryos per minute with a nucleic acid from the nucleic acid samples, such that at least 30% of injected embryos become fertile adults.

2. The method of claim 1, wherein the step of obtaining comprises obtaining at least 10 different nucleic acid samples.

3. The method of claim 1, wherein individual nucleic acid samples within the plurality contain the same nucleic acid construct.

4. The method of claim 1, where each nucleic acid sample within the plurality contains a different nucleic acid construct.

5. The method of claim 1, wherein about 40% of injected embryos survive to adulthood.

6. The method of claim 1, wherein the step of injecting comprises:
injecting through an intact chorion.

7. The method of claim 1, wherein the step of obtaining further comprises purifying the nucleic acid samples.

8. The method of claim 7, wherein the step of purifying comprises:
binding the nucleic acid samples to filters;
washing the filters with washing buffer;
applying a vacuum to the bottom of the filters;
centrifuging the filters; and
applying a vacuum to the top of the filters;
allowing the filters to air dry; and
eluting the nucleic acid samples from the filter with elution buffer.

9. The method of claim 1, wherein all steps are performed at temperatures ranging between approximately 20° C. and approximately 23° C.

10. The method of claim 1, wherein about 10 embryos are injected per minute.

11. The method of claim 1, wherein each nucleic acid sample comprises at least one construct that directs P-element-mediated transformation.

12. The method of claim 1, wherein each nucleic acid sample comprises a construct that directs integrase-mediated transformation.

13. The method of claim 1, wherein the nucleic acid samples comprise nucleic acids at a concentration less than 200 ng/μl.

* * * * *